(12) United States Patent
McElhaney, Jr.

(10) Patent No.: US 11,497,626 B2
(45) Date of Patent: *Nov. 15, 2022

(54) SHOULDER ARTHROPLASTY SYSTEM METHOD WITH COMBINATION HUMERAL SIZER, TRIAL, AND GUIDE

(71) Applicant: DePuy Synthes Products, Inc., Raynham, MA (US)

(72) Inventor: Patrick McElhaney, Jr., Bloomington, IN (US)

(73) Assignee: DePuy Synthes Products, Inc., Raynham, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/988,225

(22) Filed: Aug. 7, 2020

(65) Prior Publication Data
US 2020/0368039 A1    Nov. 26, 2020

Related U.S. Application Data

(60) Continuation of application No. 16/008,934, filed on Jun. 14, 2018, now Pat. No. 10,765,534, which is a
(Continued)

(51) Int. Cl.
*A61F 2/40* (2006.01)
*A61F 2/46* (2006.01)
*A61F 2/30* (2006.01)

(52) U.S. Cl.
CPC .......... *A61F 2/4684* (2013.01); *A61F 2/4003* (2013.01); *A61F 2/4014* (2013.01); *A61F 2/40* (2013.01); *A61F 2002/3085* (2013.01); *A61F 2002/30604* (2013.01); *A61F 2002/30616* (2013.01); *A61F 2002/4007* (2013.01);
(Continued)

(58) Field of Classification Search
CPC ........ A61F 2/4684; A61F 2/40; A61F 2/4003; A61F 2/4014; A61F 2002/4018; A61F 2002/4007; A61F 2002/4051; A61F 2002/4677; A61F 2002/30604; A61F 2002/30616; A61F 2002/3085
See application file for complete search history.

(56) References Cited

U.S. PATENT DOCUMENTS

| 7,537,618 B2 | 5/2009 | Collazo |
| 2005/0256583 A1* | 11/2005 | Bouttens ............... A61F 2/4081 623/19.13 |

(Continued)

*Primary Examiner* — Dinah Baria
(74) *Attorney, Agent, or Firm* — Maginot, Moore & Beck LLP

(57) ABSTRACT

A shoulder arthroplasty kit includes a combination sizer and guide device with a base portion including a rim configured to be positioned against a resected surface of a humerus. A cavity which is configured to receive a mounting portion of a humeral base component extends proximally from the base portion, the cavity. The combination sizer and guide device includes a convex outer surface which replicates at least a part of an outer bearing surface of a humeral head component. A bore which is perpendicular to the distal plane extends between the cavity and the convex outer surface. The kit further includes a guide pin with a maximum diameter sized to fit within the bore such that the guide pin is guided by the bore during insertion of the guide pin into the resected surface of the humerus.

14 Claims, 7 Drawing Sheets

Related U.S. Application Data division of application No. 14/807,092, filed on Jul. 23, 2015, now Pat. No. 10,016,288.

(52) U.S. Cl.
CPC ............ *A61F 2002/4018* (2013.01); *A61F 2002/4051* (2013.01); *A61F 2002/4677* (2013.01)

(56) References Cited

U.S. PATENT DOCUMENTS

| | | |
|---|---|---|
| 2011/0054478 A1 | 3/2011 | Vanasse et al. |
| 2011/0224673 A1 | 9/2011 | Smith |
| 2012/0239042 A1 | 9/2012 | Lappin et al. |
| 2015/0250601 A1 | 9/2015 | Humphrey |

\* cited by examiner

SHOULDER ARTHROPLASTY SYSTEM METHOD WITH COMBINATION HUMERAL SIZER, TRIAL, AND GUIDE

CROSS-REFERENCE TO RELATED APPLICATIONS

This application is a continuation application of copending U.S. application Ser. No. 16/008,934, entitled "SHOULDER ARTHROPLASTY SYSTEM WITH COMBINATION HUMERAL SIZER, TRIAL, AND GUIDE", filed Jun. 14, 2018, which issued Sep. 8, 2020 as U.S. Pat. No. 10,765,534 and which is a divisional application U.S. application Ser. No. 14/807,092, entitled filed Jul. 23, 2015, which issued Jul. 10, 2018 as U.S. Pat. No. 10,016,288, the contents of which are each incorporated herein by reference in their entirety.

TECHNICAL FIELD OF THE INVENTION

The present invention relates generally to the field of orthopedics, and, more particularly, to shoulder arthroplasty systems and methods for using them.

BACKGROUND

As depicted in FIG. 1, a typical shoulder or glenohumeral joint is formed in a human body where the humerus 10 movably contacts the scapula 12. The scapula 12 includes a glenoid fossa 14 that forms a socket against which the head 26 of the humerus 10 articulates. At this socket, the scapula 12 includes cartilage 16 that facilitates such articulation. Beneath the cartilage is subchondral bone 18 that forms a wall of a glenoid vault 20 that defines a cavity which contains cancellous bone 22. The subchondral bone 18 that forms the glenoid vault 20 defines a glenoid rim 24 at a periphery of the glenoid vault 20 that is attached to the cartilage 16. During the lifetime of a patient, the glenoid fossa 14 and/or the head 26 may become worn, especially at their posterior and/or superior portions thereby causing severe shoulder pain and limiting the range of motion of the patient's shoulder joint. To alleviate such pain and increase the patient's range of motion, a shoulder arthroplasty may be performed. Arthroplasty is the surgical replacement of one or more bone structures of a joint with one or more prostheses.

The goal of shoulder arthroplasty is to restore normal kinematics to the shoulder. Accordingly, known systems attempt to replicate the normal kinematics by carefully controlling the geometry of the articulating surfaces in the joint as well as the positioning of the prostheses in the bones in which the prostheses are implanted. Thus, the articulating surface of a humeral component is typically spherical, and positioning of the humeral component is accomplished by using the anatomical neck of the humerus as the reference plane for reconstruction of the humeral head.

In general, the head 26 of the humerus 10 may be resected using a saw or chisel and then planed flat. With the resected head 26 of the humerus 10 exposed, a drill guide pin may be used to insert a guide pin substantially through the center of the plane formed by resecting the head 26 of the humerus 10. The guide pin may then be used to guide subsequent instruments in the removal of bone from the humerus 10 in preparation for the insertion of a base portion of a humeral component. The guide pin may then be removed, and a base portion of a humeral component may then be inserted into the cavity. The final humeral head component size may then be determined by trialing one or more trial humeral head components on the base and performing a trial reduction of the joint. Once a trial reduction has been successfully performed, the trial head component may be removed, and the final head component may be mounted to the base.

While the foregoing procedure is generally effective, there are some drawbacks. As an initial matter, the guide pin is placed prior to positioning a trial head component on the humerus. Accordingly, the guide pin may not be optimally located. Additionally, a number of different instruments are required throughout the process. As the number of instruments increases, the cost and complexity of the procedure increases.

There remains a need for a shoulder arthroplasty system that provides for improved visualization of the head component position prior to implanting a base component. There is a further need for a shoulder arthroplasty system that facilitates positioning the base component. A shoulder arthroplasty system that reduces the number of instruments is also needed.

SUMMARY OF THE INVENTION

The present invention in one embodiment provides a shoulder arthroplasty system including a combination device with a base portion defining a distal plane, a cavity extending proximally from the base portion, the cavity configured to receive a mounting portion of a humeral base component, a convex outer surface, the convex outer surface sized to replicate at least in part an outer bearing surface of a humeral head component, and a bore extending between the cavity and the convex outer surface.

In another embodiment, a shoulder arthroplasty system includes a combination device including a base portion defining a distal plane, a cavity extending proximally from the base portion, the cavity configured to receive a mounting portion of a humeral base component, a convex outer surface, the convex outer surface sized and shaped to replicate at least in part an outer bearing surface of a humeral head component, and a bore extending between the cavity and the convex outer surface, and a guide pin sized to fit within the bore.

In another embodiment, a method of implanting a humeral component includes accessing a humerus, resecting a head portion of the humerus to form a resected surface, selecting a combination device having an outer surface sized complementary to a desired implant head size from a group of differently sized combination devices, positioning the selected combination device on the resected surface, guiding placement of a guide pin with the combination device, guiding a reamer with the guide pin to form a reamed cavity in the humerus, positioning an anchoring portion of an implant base portion in the reamed cavity, positioning the combination device on the base portion, removing the combination device from the base portion, and positioning an implant head on the base portion.

The above-noted features and advantages of the present invention, as well as additional features and advantages, will be readily apparent to those skilled in the art upon reference to the following detailed description and the accompanying drawings, which include a disclosure of the best mode of making and using the invention presently contemplated.

DETAILED DESCRIPTION

Figure 1:
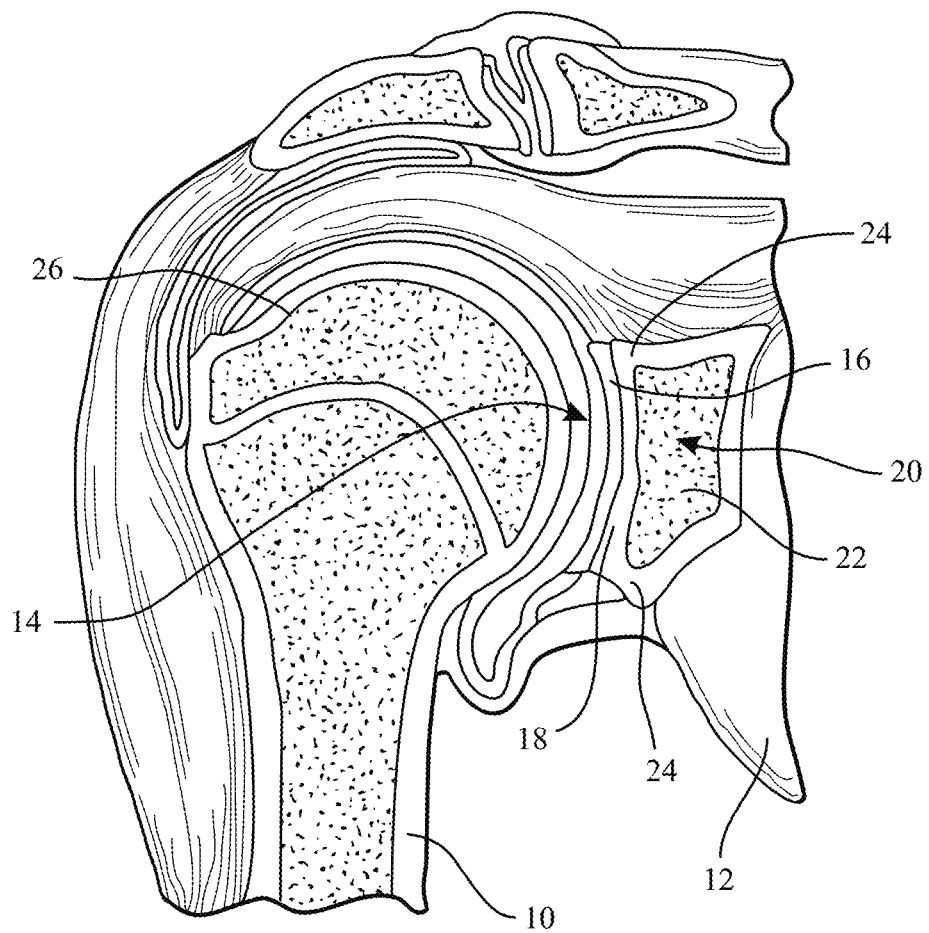
FIG. 1 depicts a coronal view of an anatomically normal shoulder joint.

Like reference numerals refer to like parts throughout the following description and the accompanying drawings.

Figure 2:
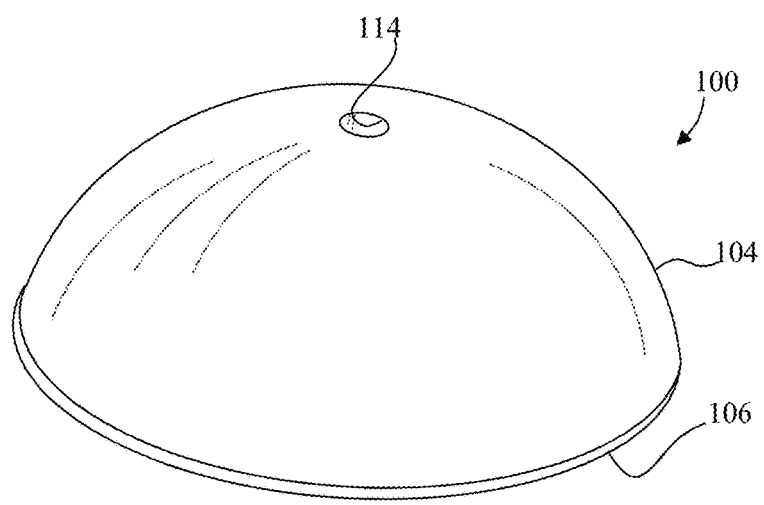
FIG. 2 depicts a top perspective view of a combination sizer and guide device in accordance with principles of the disclosure.
Figure 3:
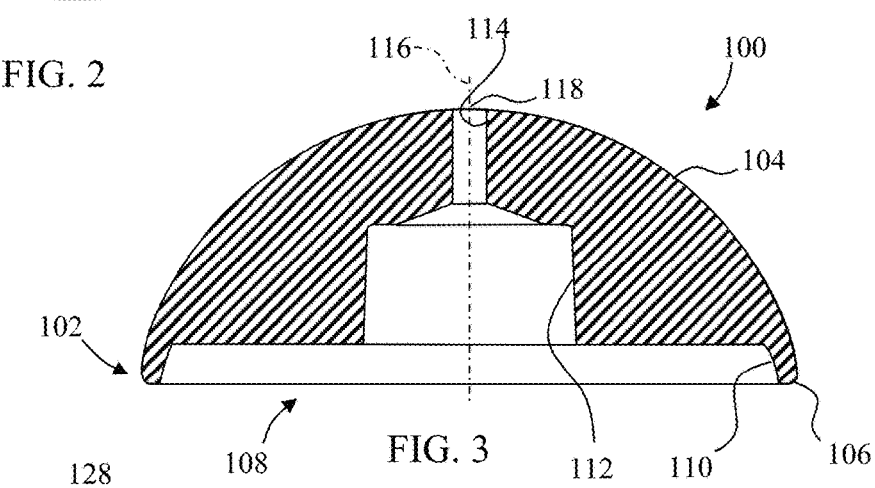
FIG. 3 depicts a side cross-sectional view of the combination device of FIG. 2.

FIGS. 2-3 depict a combination device 100. The combination device 100 includes base portion 102 and a convex outer surface 104 which in this embodiment is hemispherically shaped. A rim 106 of the base portion 102 is generally planar distally as depicted in the view of FIG. 3. A cavity 108 extends proximally from the rim 106. The cavity 108 includes a mouth portion 110 and an upper cavity portion 112. A guide bore 114 extends between the upper cavity portion 112 and the convex outer surface 104. In the embodiment of FIGS. 2 and 3, the guide bore 114 defines an axis 116 which is perpendicular to the plane defined by the rim 106. The guide bore 114 is centered at a zenith 118 of the outer surface 104.

The outer surface 104 is shaped complementary to an associated humeral head component. Specifically, the curvature of the outer surface 104 is identical to the curvature of a humeral head component as discussed more fully below. In the embodiment of FIGS. 2-3, the outer surface 104 is shaped identically to the outer surface of a humeral head component with the exception of the opening of the bore 114 to the outer surface 104.

Figure 4:
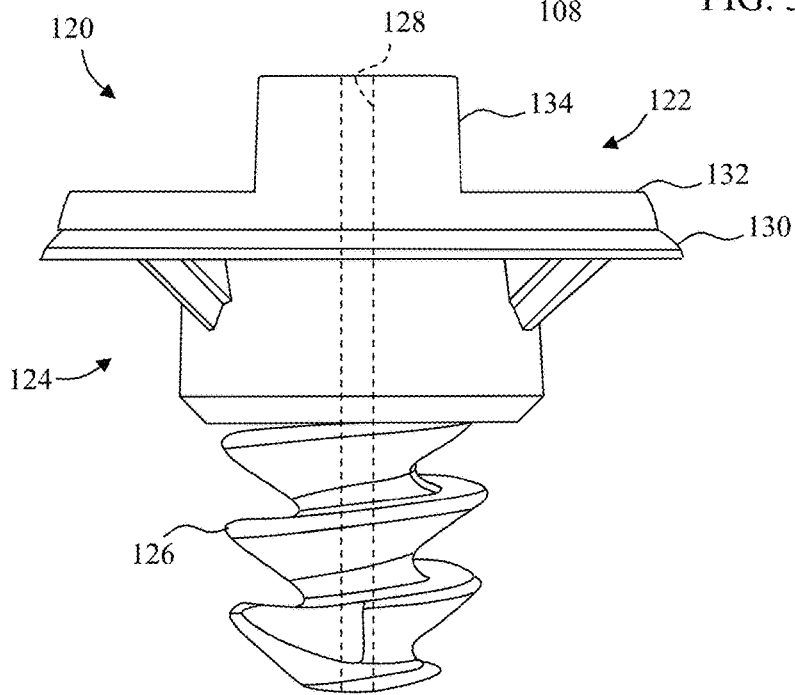
FIG. 4 depicts a side plan view of a humeral base component that in some embodiments is included in a kit along with the combination device of FIG. 2 and which includes a mounting portion which mates with the combination device of FIG. 2.

The upper cavity portion 112 is shaped complementary to a mounting portion of a humeral base component. By way of example, FIG. 4 depicts a humeral base component 120 which can be used with the combination device 100. The base component 120 includes a mounting portion 122, an anchoring portion 124, and a fixation member 126. A guide bore 128 extends completely through the mounting portion 122, the anchoring portion 124, and the fixation member 126. A flange 130 is located at a proximal portion of the anchoring portion 124 and is located distally of a mating portion 132 of the mounting portion 122. A taper portion 134 of the mounting portion 122 extends proximally from the mating portion 132.

The combination device 100 in this embodiment is an integrally formed unit made from a durable biocompatible plastic, metal, alloy, or any other suitable durable biocompatible material. For example, the combination device 100 may be made from a polyethylene.

Figure 5:
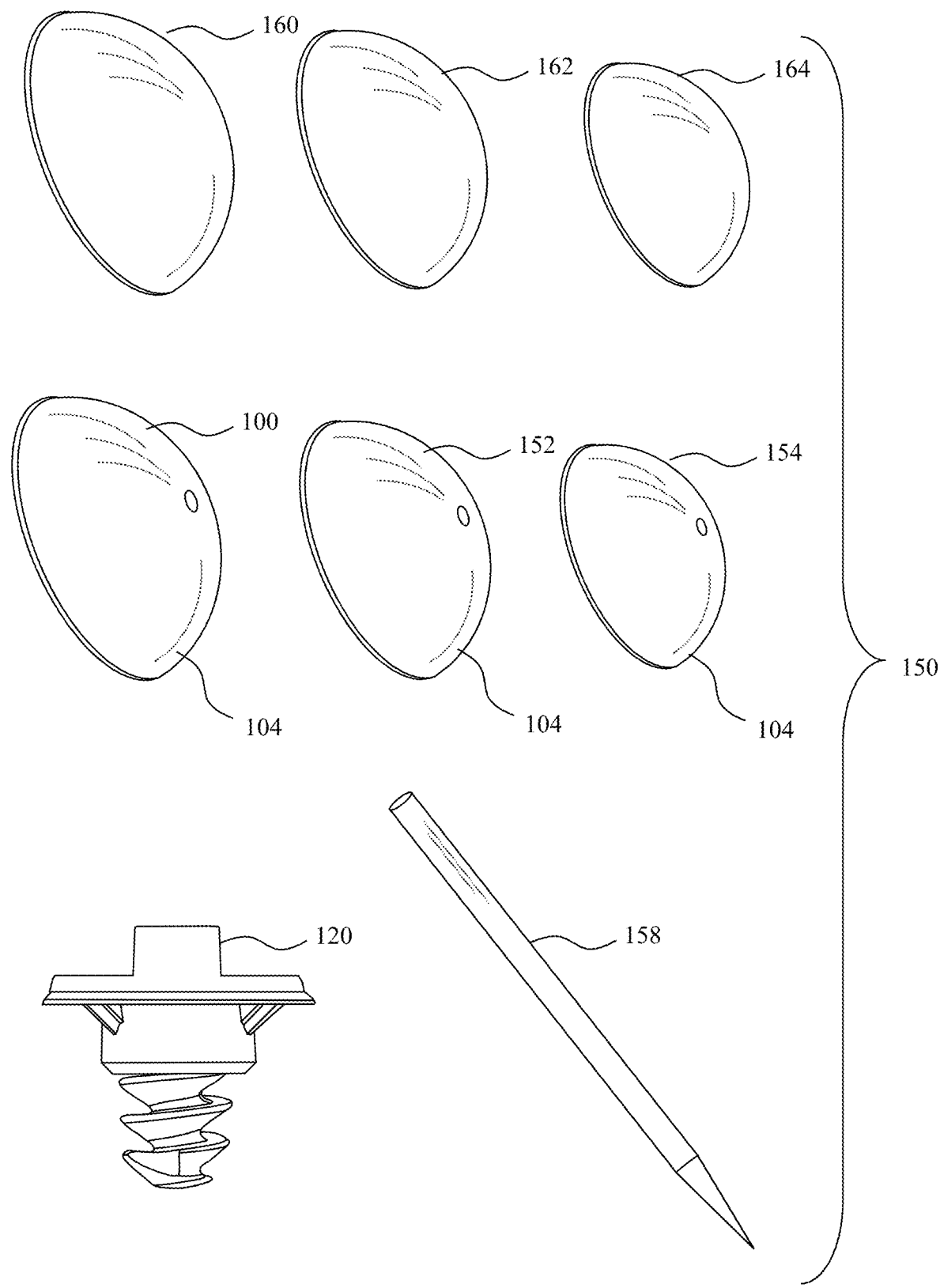
FIG. 5 depicts a kit including a number of combination devices and associated humeral head components, a base component, and a guide pin.

In one embodiment, the combination device 100 is provided in a system used in shoulder arthroplasty along with a humeral base component such as the base component 120. FIG. 5 depicts one such system in the form of kit 150 which includes combination devices 100, 152, and 154, the base component 120, a guide pin 158, and three humeral head components 160, 162, and 164. In one embodiment, the kit 150 includes one or more reamers (not shown) and other instrumentation for forming a cavity in a bone. For example, some embodiments of the kit 150 will include one or more of drill bits, punches, and implant inserters.

The size and shape of the outer surface 104 of each of the combination devices 100, 152, and 154 is different from the size and shape of each of the other of the combination devices 100, 152, and 154. The size and shape of the outer surface 104 of each of the combination devices 100, 152, and 154 is functionally identical to the size and shape of the articulating surface of a respective one of the humeral head components 160, 162, and 164.

Figure 6:
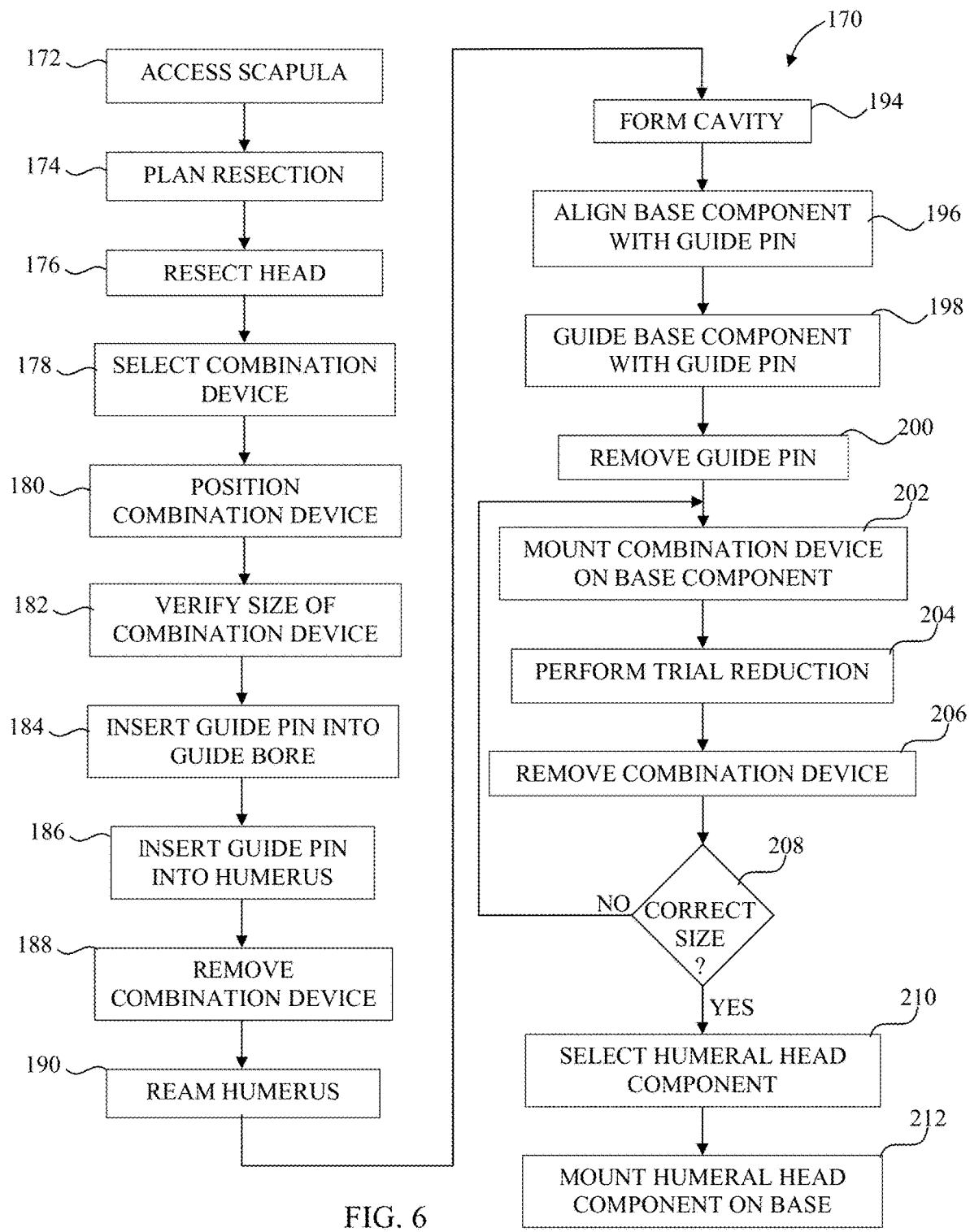
FIG. 6 depicts a procedure which uses the shoulder arthroplasty system of FIG. 5 in replacing a humeral head.
Figure 7:
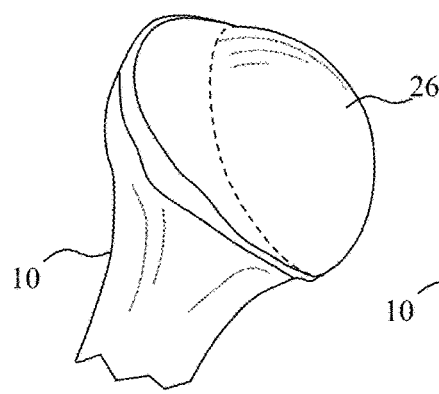
FIG. 7 depicts the humerus of FIG. 1 after the humerus has been accessed pursuant to a desired surgical approach.
Figure 8:
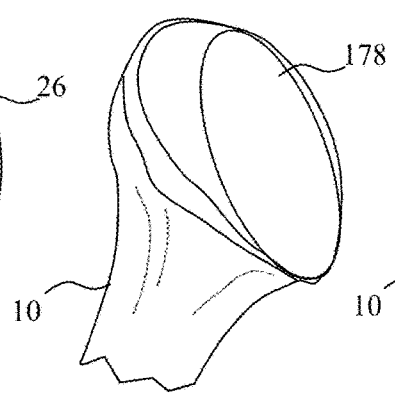
FIG. 8 depicts the humerus of FIG. 7 with the humeral head resected to form a resected plane.

The kit 150 may be used to implant a prosthesis in accordance with a procedure 170 depicted in FIG. 6. In accordance with the procedure 170, and with further reference to FIG. 7 et seq., a humerus 10 is accessed at block 172 in accordance with a desired surgical approach. At block 174, resection of all or part of the humeral head 26 is planned as depicted in FIG. 7. The humeral head 26 is then resected (block 176) leaving a substantially planar portion 178 (FIG. 8).

One of the combination devices 100, 152, and 154 is then selected at block 178. More specifically, each of the combination devices 100, 152, and 154 is sized differently from the other of the combination devices 100, 152, and 154 and each of the combination devices 100, 152, and 154 is sized identically to a respective one of the humeral head components 160, 162, and 164. Accordingly, the surgeon selects the combination device 100, 152, or 154 corresponding to the desired size of humeral head component 160, 162, or 164 which is expected to be implanted.

Figure 9:
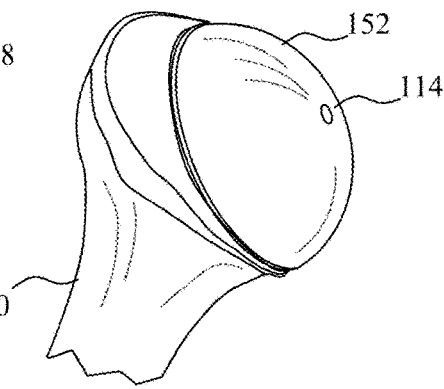
FIG. 9 depicts the humerus of FIG. 8 with one of the combination devices of FIG. 5 positioned on the resected plane to allow a surgeon to visualize the finally implanted humeral implant.
Figure 10:
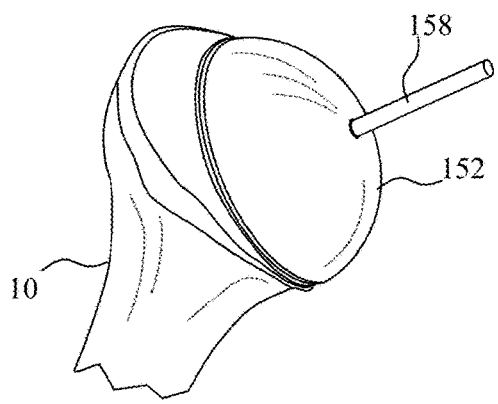
FIG. 10 depicts the combination device of FIG. 9 used to guide implantation of a guide pin into the resected plane of the humerus.

The selected combination device (combination device 152 in this example) is then positioned on the planar portion 178 as depicted in FIG. 9 (block 180). The surgeon then determines if the selected combination device is the optimal size based upon an assessment of the specific humerus and glenoid (block 182). If upon positioning the selected combination device on the planar portion 178 the surgeon determines that the selected combination device has an incorrect size, then the combination device is removed and a different combination device is selected. Thus, if the combination device 152 is too large, then the combination device 152 is removed and the combination device 100 is positioned on the planar portion 178. If the combination device 152 is too small, then the combination device 152 is removed and the combination device 154 is positioned on the planar portion 178. When the surgeon is satisfied with the size of the selected combination device and with the positioning of the combination device on the planar portion 178, the guide pin 158 is inserted into the guide bore 114 (FIG. 10 and block 184).

Figure 11:
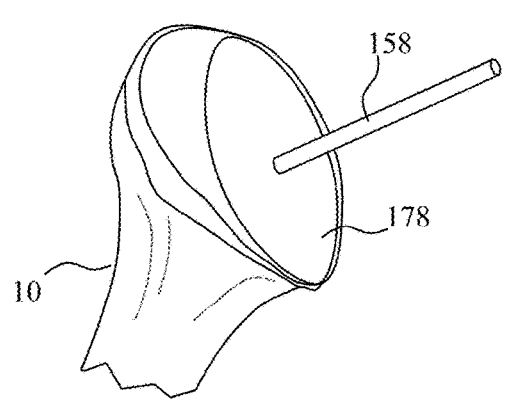
FIG. 11 depicts the humerus and guide pin of FIG. 10 after the combination device has been removed for a first time.

The guide bore 114 is sized to slidingly receive the guide pin 158. Additionally, the guide bore 114 is positioned and oriented such that by inserting the guide pin 158 through the guide bore 114, the guide pin 158 is directed to the center of the portion of the planar portion 178 which is covered by the combination device 152. The guide bore 114 is then used to guide insertion of the guide pin 158 into the humerus 10 (block 186). In some embodiments, the guide bore 114 is further used to guide a drill bit which is used to ease insertion of the guide pin 158 into the humerus 10. The combination device 152 is then removed leaving the guide pin 158 within the humerus 10 as depicted in FIG. 11 (block 188).

Figure 12:
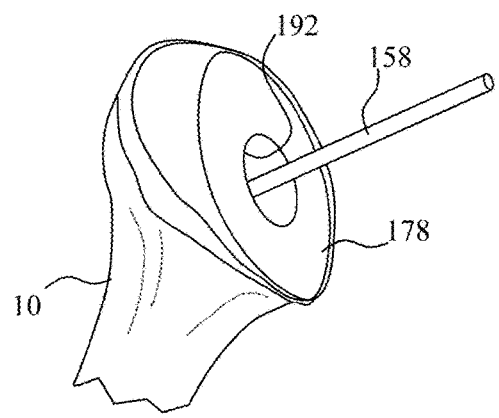
FIG. 12 depicts the humerus and guide pin of FIG. 11 after a cavity has been formed using the guide pin to guide a reamer.

The reamer (not shown) is then guided by the guide pin 158 to form a cavity 192 in the humerus. (FIG. 12 and blocks 190 and 194). In some embodiments, more than one reamer or other instrument is used to form the cavity 192. For example, one reamer may be used to form a portion of the cavity 192 that is to receive the anchoring portion 124 while another reamer or instrument is used to form a portion of the cavity 192 which is to receive the fixation member 126. The reamer(s) and other instruments will vary depending upon the particular base component in a particular kit.

Figure 14:
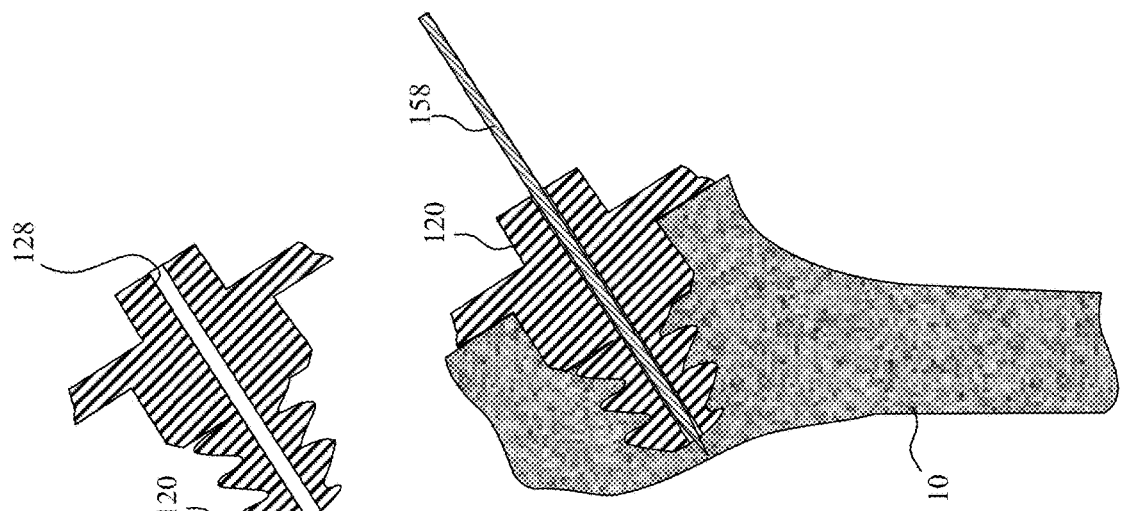
FIG. 14 depicts the base component, humerus and guide pin of FIG. 13 after the guide pin has been used to guide positioning of the base component within the cavity of the humerus.
Figure 13:
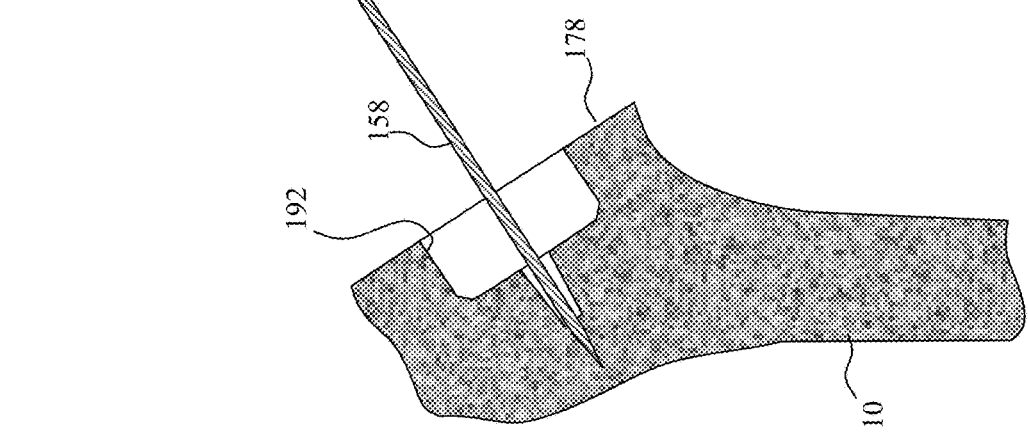
FIG. 13 depicts the base component of the kit of FIG. 5 aligned with the guide pin.

When the cavity 192 is finally prepared, the guide bore 128 of the humeral base component 120 is aligned with the guide pin 158 as shown in FIG. 13 (block 196). The guide pin 158 is then used to position the base component 120 in the cavity 192 as shown in FIG. 14 (block 198). While the kit 150 only depicts a single base component 120, in some embodiments a variety of base component configuration will be provided, e.g., differently sized fixation members, different types of fixation members, etc. The kit is further modified to include reamers, punches, etc. consistent with the additional base components.

Figure 15:
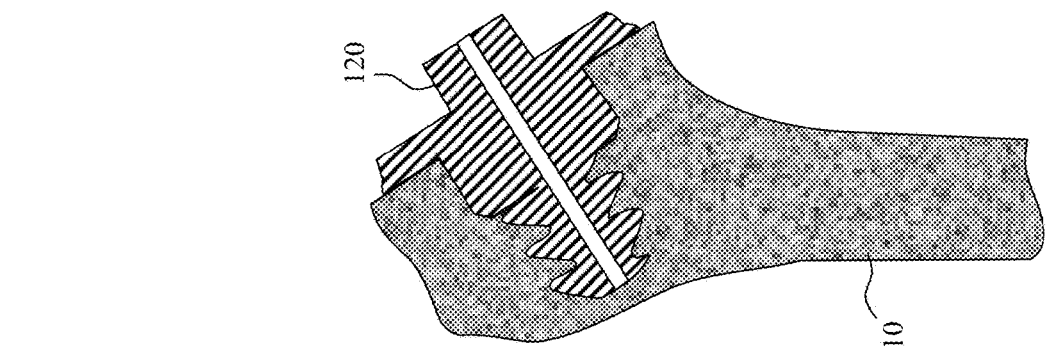
FIG. 15 depicts the humerus and base component of FIG. 14 with the guide pin removed.
Figure 16:
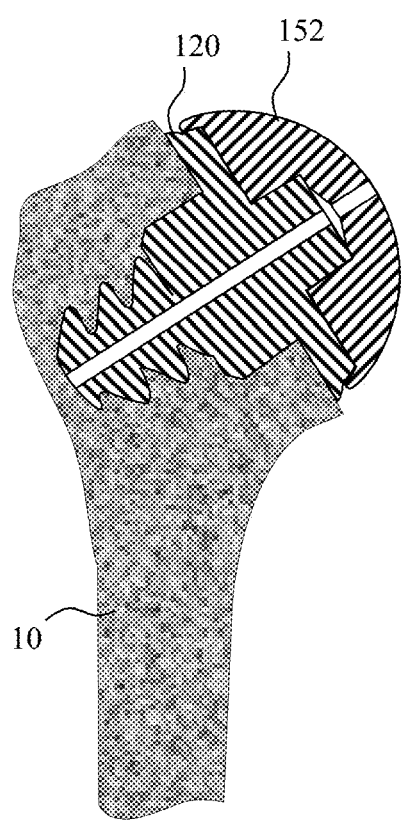
FIG. 16 depicts the humerus and base component of FIG. 14 with the combination device of FIG. 10 temporarily mounted on the base component.

Returning to the procedure 170, the guide pin 158 is then removed resulting in the condition of FIG. 15 (block 200). With the guide pin 158 removed, the previously selected combination device (combination device 152 in this example) is positioned on the base component 120 as shown in FIG. 16 (block 202). The cavity 108 of the combination device 152 is sized to frictionally fit on the mounting portion 122. In some embodiments, only the mouth portion 110 frictionally engages the mating portion 132. In some embodiments only the upper cavity portion 112 frictionally engages the taper portion 134. In some embodiments both the mouth portion 110 and the upper cavity portion 112 frictionally engage the mating portion 132 and the taper portion 134, respectively.

In all of the embodiments, the engagement between the combination device and the base component is not permanent, but is sufficient to allow a trial reduction. Accordingly, once the combination device is mounted on the base component, the surgeon performs a trial reduction (block 204).

The surgeon assesses the trial reduction and then removes the combination device resulting in the configuration that was shown in FIG. 15 (block 206).

If the combination device was determined to not be the optimum size during the trial reduction, the process returns to block 202 from block 208. If the combination device 152 is too large, then the surgeon removes the combination device 152 (block 206) and repeats blocks 202 and 204 by selecting a smaller combination device such as the combination device 100, mounting the combination device 100 on the base component 120, and performing another trial reduction. If the combination device 152 is too small, then the surgeon removes the combination device 152 (block 206) and repeats blocks 202 and 204 by selecting a larger combination device such as the combination device 154, mounting the combination device 154 on the base component 120, and performing another trial reduction. In the embodiment of FIG. 5, only three combination devices are shown. In some embodiments, there are fewer combination devices while in other kits there are more. In all of these embodiments, the surgeon continues blocks 202 and 204 as necessary to obtain the desired size.

Figure 17:
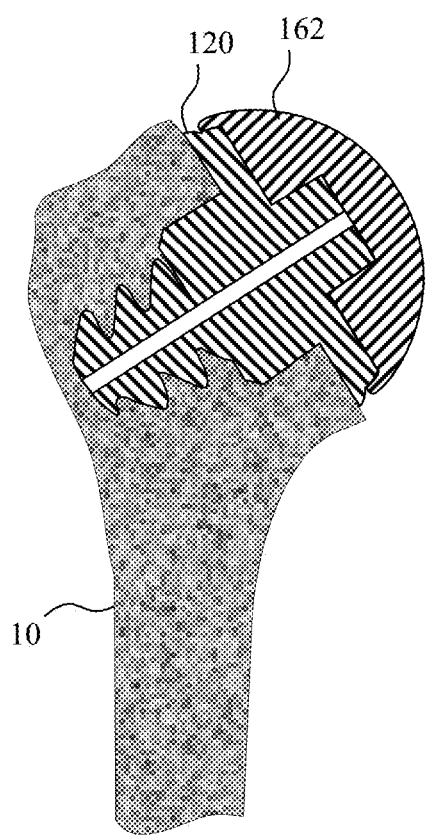
FIG. 17 depicts the humerus and base component of FIG. 16 with the combination device replaced by a humeral head component associated with the removed combination device.

If at block 208 the desired combination device size has been finally determined, the surgeon then selects the humeral head component that is associated with the optimally sized combination device (block 210). Thus, if the combination device 152 is the optimally sized combination device as determined during the trial reduction, the surgeon selects the humeral head component 162. Once the associated humeral head component is selected, the surgeon mounts the selected humeral head component on the base component at block 212 (see FIG. 17). In the embodiment of FIG. 5, each of the humeral head components 160, 162, and 164 are configured to form a taper lock with the taper portion 134 of the base component 120.

The procedure 170 may be modified in a number of ways. By way of example, while in the above example the guide pin was removed prior to mounting the combination device on the base component, in some embodiments the combination device is mounted prior to removal of the guide pin. Additionally, the base component in some embodiments does not include a guide bore. In such embodiments, the guide pin is removed prior to implanting the base component. In some embodiments, the guide pin is used to guide a punch and/or a drill instead of or in addition to the reamer. The punch in some embodiments is used to prepare the humerus to receive pegs, fins, or other portions of a base component. In some embodiments, the humeral head component includes a guide bore allowing the guide pin to be used to position the humeral head component prior to removal of the guide pin.

The foregoing description of the invention is illustrative only, and is not intended to limit the scope of the invention to the precise terms set forth. Further, although the invention has been described in detail with reference to certain illustrative embodiments, variations and modifications exist within the scope and spirit of the invention as described and defined in the following claims.

What is claimed is:

1. A shoulder arthroplasty kit comprising: a humeral base component;
   a guide pin configured to be inserted into a resected surface of a humerus; and
   at least one combination sizer and guide device including
      a base portion including a distal rim configured to be positioned against the resected surface of the humerus and defining a distal plane, a cavity extending proximally from the base portion, the cavity configured to receive a mounting portion of the humeral base component, a convex outer surface configured to replicate at least in part an outer bearing surface of a humeral head component, and a bore extending between the cavity and the convex outer surface, the bore perpendicular to the distal plane and configured to guide the guide pin such that when the distal rim is positioned against the resected surface the guide pin is guided by the bore during insertion of the guide pin through the bore such that the guide pin is directed to a center portion of into the resected surface of the humerus which is covered by the base portion; wherein the humeral base component includes a taper portion extending upwardly from the mounting portion; the combination sizer and guide device includes an upper cavity extending upwardly from the cavity toward the convex outer surface; and the upper cavity is sized and shaped to frictionally engage the taper portion.

2. The kit of claim 1, wherein:

the at least one combination sizer and guide device comprises a first and a second combination sizer and guide device;

the first combination sizer and guide device has a first size;

the second combination sizer and guide device has a second size; and the first size is different from the second size.

3. The kit of claim 1, wherein:

the at least one combination sizer and guide device comprises a first and a second combination sizer and guide device;

the first combination sizer and guide device has a first shape;

the second combination sizer and guide device has a second shape; and the first shape is different from the second shape.

4. The kit of claim 1, further comprising:

at least one humeral head component, the at least one humeral head component including a mating portion sized and shaped to mate with the mounting portion.

5. The kit of claim 4, the humeral base component further comprising:

a guide bore, the guide bore having a minimum diameter that is larger than the maximum diameter of the guide pin.

6. The kit of claim 5, wherein the guide bore extends completely through the humeral base component.

7. The kit of claim 4, wherein the humeral base component further comprises:

an anchoring portion located beneath the mounting portion, the anchoring portion having a maximum diameter that is smaller than a maximum diameter of the mounting portion;

a threaded portion extending distally from the anchoring portion; and a guide bore extending through the mounting portion, the anchoring portion, and the threaded portion, the guide bore having a minimum diameter that is larger than the maximum diameter of the guide pin.

8. A shoulder arthroplasty kit comprising: a humeral base component;

a guide pin configured to guide a reamer during reaming of a humerus, and configured to be inserted into a resected surface of the humerus; and at least one combination sizer and guide device including a base portion including a distal rim configured to be positioned against the resected surface of the humerus and defining a distal plane, a cavity extending proximally from the base portion, the cavity configured to receive a mounting portion of the humeral base component, a convex outer surface configured to replicate at least in part an outer bearing surface of a humeral head component, and a bore extending between the cavity and the convex outer surface, the bore perpendicular to the distal plane, and configured to receive the guide pin within the bore such that the guide pin is guided by the bore during insertion of the guide pin into the resected surface of the humerus; wherein the humeral base component includes a taper portion extending upwardly from the mounting portion; the combination sizer and guide device includes an upper cavity extending upwardly from the cavity toward the convex outer surface; and the upper cavity is sized and shaped to frictionally engage the taper portion.

9. The kit of claim 8, wherein:

the at least one combination sizer and guide device comprises a first and a second combination sizer and guide device;

the first combination sizer and guide device has a first size;

the second combination sizer and guide device has a second size; and the first size is different from the second size.

10. The kit of claim 8, wherein:

the at least one combination sizer and guide device comprises a first and a second combination sizer and guide device;

the first combination sizer and guide device has a first shape;

the second combination sizer and guide device has a second shape; and the first shape is different from the second shape.

11. The kit of claim 8, further comprising:

at least one humeral head component, the at least one humeral head component including a mating portion sized and shaped to mate with the mounting portion.

12. The kit of claim 11, the humeral base component further comprising:

a guide bore, the guide bore having a minimum diameter that is larger than the maximum diameter of the guide pin.

13. The kit of claim 12, wherein the guide bore extends completely through the humeral base component.

14. The kit of claim 11, wherein the humeral base component further comprises:

an anchoring portion located beneath the mounting portion, the anchoring portion having a maximum diameter that is smaller than a maximum diameter of the mounting portion;

a threaded portion extending distally from the anchoring portion; and a guide bore extending through the mounting portion, the anchoring portion, and the threaded portion, the guide bore having a minimum diameter that is larger than the maximum diameter of the guide pin.

* * * * *